US011161657B2

(12) United States Patent
Hawry et al.

(10) Patent No.: US 11,161,657 B2
(45) Date of Patent: Nov. 2, 2021

(54) CHILD RESISTANT SENIOR FRIENDLY BOTTLE PACKAGING FOR LIQUIDS

(71) Applicant: Berlin Packaging, LLC, Chicago, IL (US)

(72) Inventors: Liam Hawry, Chicago, IL (US); Alex Garfield, Chicago, IL (US)

( * ) Notice: Subject to any disclaimer, the term of this patent is extended or adjusted under 35 U.S.C. 154(b) by 0 days.

(21) Appl. No.: 17/064,619

(22) Filed: Oct. 7, 2020

(65) Prior Publication Data

US 2021/0155386 A1 May 27, 2021

Related U.S. Application Data

(63) Continuation-in-part of application No. 16/693,839, filed on Nov. 25, 2019, now Pat. No. 10,875,688.

(51) Int. Cl.
*B65D 50/06* (2006.01)
*B65D 41/26* (2006.01)
*A61M 5/24* (2006.01)

(52) U.S. Cl.
CPC ............. *B65D 50/061* (2013.01); *A61M 5/24* (2013.01); *B65D 41/26* (2013.01); *B65D 2203/04* (2013.01); *B65D 2215/04* (2013.01)

(58) Field of Classification Search
CPC ...... B65D 50/043; B65D 47/20; A61J 1/1412; G01F 11/028
USPC .................................................. 222/153.01
See application file for complete search history.

(56) References Cited

U.S. PATENT DOCUMENTS

| | | |
|---|---|---|
| 333,250 A | 12/1885 | Pell |
| 1,453,445 A | 2/1922 | Covell |
| 1,684,313 A | 3/1927 | Graham |
| 3,767,088 A | 10/1973 | Deussen |
| 4,072,247 A | 2/1978 | Yamazaki |
| 4,399,920 A | 8/1983 | Swartzbaugh et al. |
| 4,445,626 A | 5/1984 | Steffen et al. |
| 4,498,904 A | 2/1985 | Turner et al. |
| 4,526,294 A | 7/1985 | Hirschmann et al. |
| 4,936,490 A | 6/1990 | Battegazzore |
| 4,962,868 A | 10/1990 | Borchard |
| 5,746,349 A * | 5/1998 | Putteman ............. G01F 11/027 222/49 |
| 5,950,690 A | 9/1999 | Seidler |

(Continued)

FOREIGN PATENT DOCUMENTS

| | | |
|---|---|---|
| EP | 0723921 | 7/1996 |
| EP | 0706487 | 9/2000 |

(Continued)

OTHER PUBLICATIONS cooljarz.com/products/crringe-child-resistant-syringe-in-a-bottle; May 16, 2015.

(Continued)

*Primary Examiner* — Vishal Pancholi
(74) *Attorney, Agent, or Firm* — Adam K. Sacharoff; Much Shelist, P.C

(57) ABSTRACT

In one embodiment there is provided a bottle assembly to dispense a liquid. The assembly includes a bottle, a syringe, a cap and collar. The assembly includes a child-resistant adult-friendly retaining portion to permit the removal of the cap and collar. The syringe is configured to draw liquid from the bottle at a precise dosage and then when the cap and collar is removed the user can expel the liquid.

5 Claims, 22 Drawing Sheets

(56) References Cited

U.S. PATENT DOCUMENTS

| | | | |
|---|---|---|---|
| 6,112,779 A * | 9/2000 | Camilla | A61J 1/2096 141/22 |
| 6,250,504 B1 * | 6/2001 | Maffei | A61J 1/2096 141/381 |
| 6,273,152 B1 | 8/2001 | Beuhler et al. | |
| 6,609,635 B1 * | 8/2003 | Maffei | G01F 11/025 222/309 |
| 6,770,056 B2 * | 8/2004 | Price | G01F 11/023 222/43 |
| 8,403,008 B2 * | 3/2013 | Bouix | G01F 11/025 141/27 |
| 8,851,339 B2 | 10/2014 | Schultz et al. | |
| 9,283,363 B1 | 3/2016 | Scorzelli et al. | |
| 9,427,064 B2 | 8/2016 | Kim | |
| 9,452,263 B2 * | 9/2016 | Grunhut | A61M 5/31501 |
| 2017/0231365 A1 | 8/2017 | Choi | |

FOREIGN PATENT DOCUMENTS

| | | |
|---|---|---|
| EP | 0931591 | 6/2002 |
| WO | 2000037896 | 6/2000 |
| WO | 2000060318 | 10/2000 |
| WO | 2015015390 | 2/2015 |

OTHER PUBLICATIONS raepak.com/a-new-dispensing-cap-that-will-change-the-packaging-industry/; Apr. 24, 2017.
https://www.sgh-healthcaring.com/en/accessories-for-oral-dosing-syringes/22-capsule-essuyeuse-pipette-c2-ml.html; Apr. 17, 2019.
U.S. Appl. No. 16/693,839 Corresponding CIP US Application, Office Action dated Aug. 14, 2020.

* cited by examiner

CHILD RESISTANT SENIOR FRIENDLY BOTTLE PACKAGING FOR LIQUIDS

CROSS REFERENCE OF PRIOR APPLICATIONS

The present invention is a Continuation In Part of U.S. application Ser. No. 16/693,839 filed on Nov. 25, 2019.

FIELD OF THE INVENTION

The present invention relates generally to a bottle packaging assembly for liquids to be drawn off in doses, which has a child resistant senior friendly functionality.

BACKGROUND OF THE INVENTION

Bottle assemblies typically include a closure that may contain a pharmaceutical or nutritional product within a bottle or other container such as a liquid. These bottle assemblies essentially include a syringe means, with a piston associated with a cap that is maneuverable from the outside for sucking the liquid into the syringe. Markers on the outside of the cap is provided by means of which it is possible to assess from the outside the volume of liquid drawn. While these are aspects known in the industry, the prior art is devoid of unique "child-resistant" features that make the cap difficult for children to turn. It would be desirable to construct and implement an extremely simple push down and turn child resistant closure which is easy for adults to open while maintaining child resistance.

SUMMARY OF THE INVENTION

In one embodiment of the present invention there is provided a child-resistant, adult-friendly, bottle assembly to dispense a liquid. The bottle assembly includes a bottle having a neck portion defining an opening about an upper rim to create an internal reservoir for holding a liquid. A cap and collar assembly, defining a cap portion and a collar portion, is configured such that the cap portion is secured within the collar portion and vertically movable in relation to the collar portion. A child-resistant adult-friendly retaining means is configured to removably attach the cap and collar assembly to the neck portion of the bottle. The child-resistant adult-friendly retaining means is configured in a first position to lock the collar portion to the neck portion of the bottle and further configured in a second position to unlock the collar to allow the removal of the collar and cap assembly together as a unit from the bottle. Movement of the collar, separate from the vertical movement of the cap, manually being pressed down towards the bottle and rotated in a first direction unlocks the collar and cap assembly from the bottle. A syringe means is secured to the cap. The syringe means having a syringe tube positioned within the bottle when the cap and collar assembly is attached to the bottle, the syringe means is configured to draw a liquid from the bottle when the cap portion is vertically moved away from the collar portion and the cap and collar assembly is attached to the bottle, and further configured to expel a liquid from the syringe tube when the cap portion is vertically moved towards the collar portion either when the cap and collar assembly is attached to the bottle or unattached to the bottle.

The child-resistant adult-friendly bottle assembly of the present embodiment can be further defined such that the neck portion of the bottle further includes a bottom annual bead and a pair of locking lugs. The pair of locking lugs being positioned on the neck portion between the bottom annular bead and the upper rim.

The child-resistant adult-friendly bottle assembly of the present embodiment can be further defined such that the cap portion includes a top base terminating to a downwardly extending side wall. Dosage marking indicia can be positioned downwardly along the side wall and viewable on the outside of the cap portion as the cap portion is vertically moved in relation to the collar portion. The side wall can further include a bottom lip extending outwardly. The side wall can further include an indented section configured along a portion of the side wall. The indented section includes a flange extending along and attaching to an arm. The arm being wider than the flange to create channels on either side of the flange between the indented section and the arm.

The child-resistant adult-friendly bottle assembly of the current embodiment can be further defined by having the collar portion including an external cylindrical wall extending from a top rim to a bottom rim. An indented wall section defined along a section of the external cylindrical wall has a slot defined therein. The indented wall section and slot are configured to receive the flange of the cap portion with the arm of the cap portion situated externally along the indented wall section on the external cylindrical wall and the side wall of the cap portion situated internally to the indented wall section of the collar portion to create vertical movement of the cap portion in relation to the collar portion. A ledge projects inwardly from an internal surface of the external cylindrical wall and being positioned towards the top rim. The cap portion being vertically movable in relation to the collar portion with the ledge of the external cylindrical wall and the bottom lip acting together as an upper limit of movement between the cap portion and collar portion.

The child-resistant adult-friendly bottle assembly of the current embodiment can be further defined by having a dosage of liquid within the syringe tube configured to match the dosage marking indicia as the cap portion is moved and the dosage marking indicia aligns with the top rim of the collar portion.

The child-resistant adult-friendly bottle assembly of the current embodiment can be further defined by having the syringe means configured to draw and expel a liquid as the cap portion is vertically moved in relation to the collar portion. The syringe means has a syringe tube with an opening configured to rest within the bottle to draw and expel a liquid. A piston extending downwardly from an underside portion of the top base of the cap portion and a piston plug secured to the piston is used with the cap portion and collar portion.

The child-resistant adult-friendly bottle assembly of the current embodiment can be further defined by having the collar portion including a surface member extending inwardly from the external cylindrical wall. An upstanding well wall and a downwardly extending well wall both extending from the surface member define an internal well opening within the upstanding and downwardly extending well walls. The downwardly extending well wall is configured to rest within the opening of the bottle and the internal well includes radially inward lips defined as an upper lip and lower lip spaced to engage and capture a head defined on a top portion of the syringe tube. The upstanding well wall is configured to receive the piston and frictionally fit the piston plug such that movement of the cap portion and thus piston and piston plug within the upstanding well wall draws and expel liquid from the syringe tube.

The child-resistant adult-friendly bottle assembly of the current embodiment can be further defined by having a pair of latches, separately corresponding to each of the locking lugs, in the pair of locking lugs. Each locking lug includes an entrance ramp tapering downwardly towards the annual bead leading into a channel. The channel being positioned slightly higher than an end wall of the entrance ramp to create a seat between the end wall and a defined stop wall. The collar portion is locked when the latches are positioned in the seats and the collar and cap assembly is removably from the bottle when the collar portion is pressed down until the latches are below the end wall and then the collar portion is twisted to move the latches into the entrance ramp thereby releasing the collar and cap assembly from the bottle.

The child-resistant adult-friendly bottle assembly of the current embodiment can be further defined by having the pair locking lugs spaced 180° from each other around the neck portion.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein.

DETAILED DESCRIPTION OF THE DRAWINGS

Figure 1:
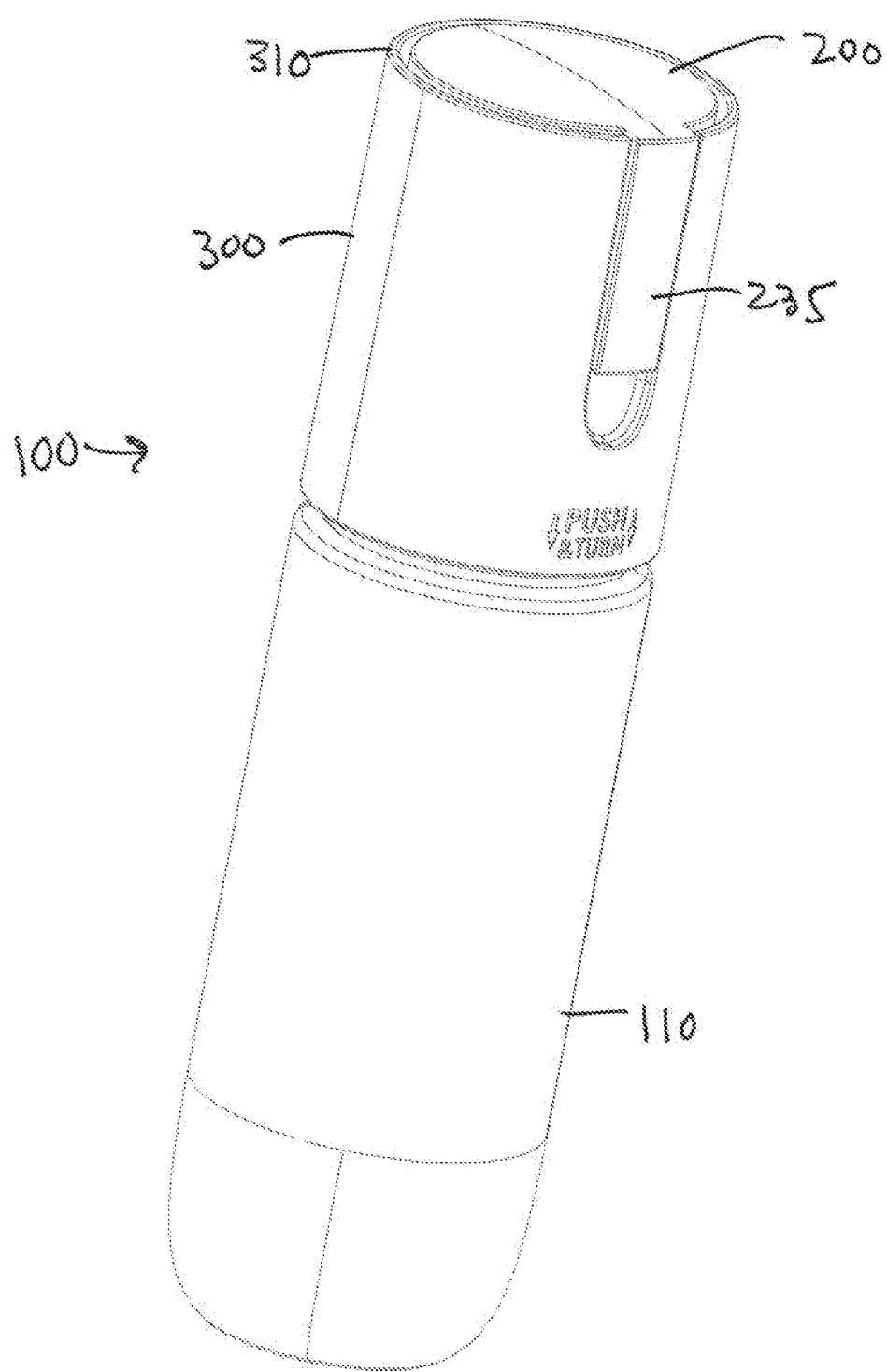
FIG. 1 is a perspective view of the bottle assembly for dosing liquids in accordance with an embodiment of the present invention.

While the invention is susceptible to embodiments in many different forms, there are shown in the drawings and will be described in detail herein the preferred embodiments of the present invention. It should be understood, however, that the present disclosure is to be considered an exemplification of the principles of the invention and is not intended to limit the spirit or scope of the invention and/or claims of the embodiments illustrated.

Figure 2:
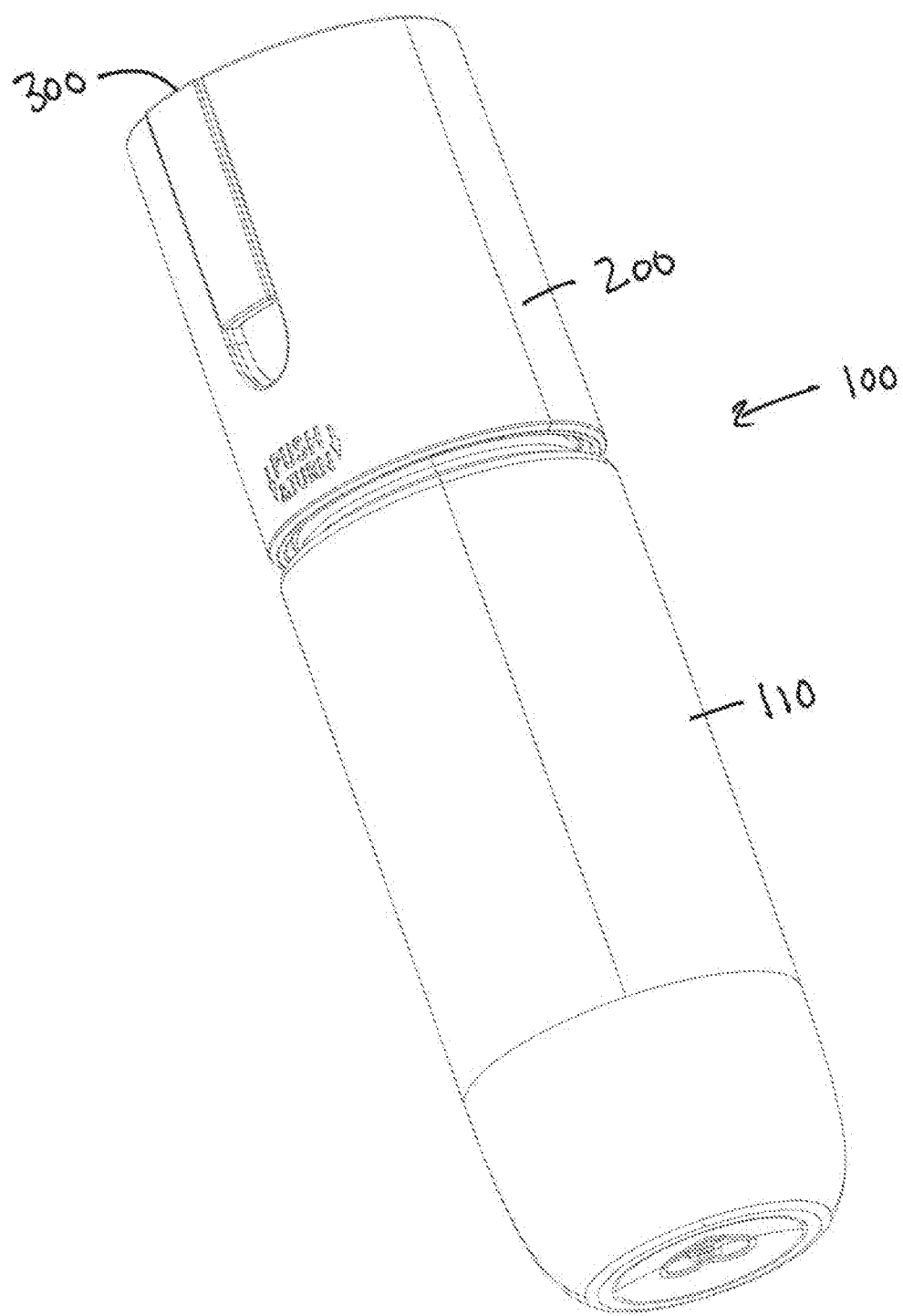
FIG. 2 is another view of the bottle assembly.
Figure 3:
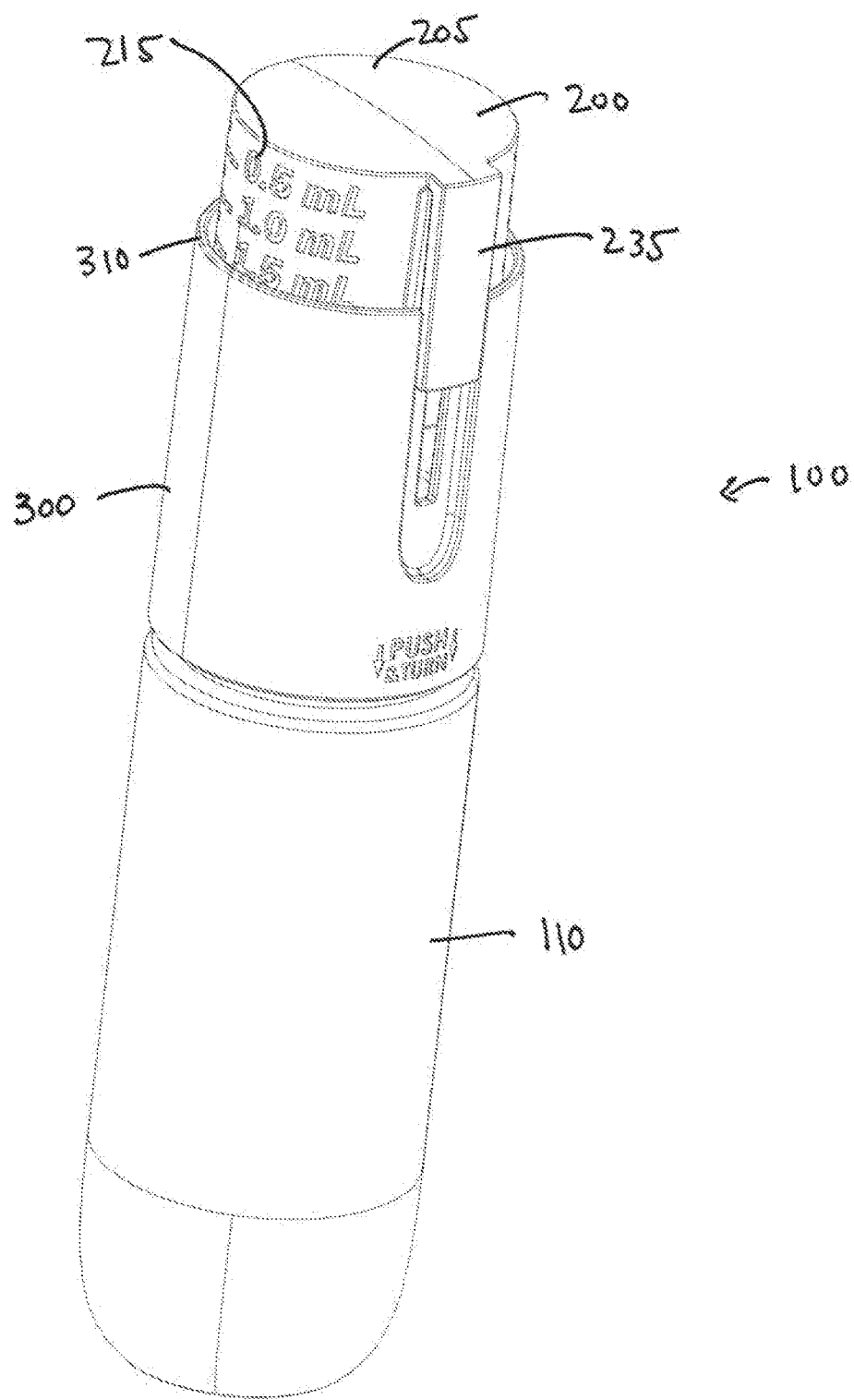
FIG. 3 is a perspective view showing the visual dosage markings on the cap.
Figure 4:
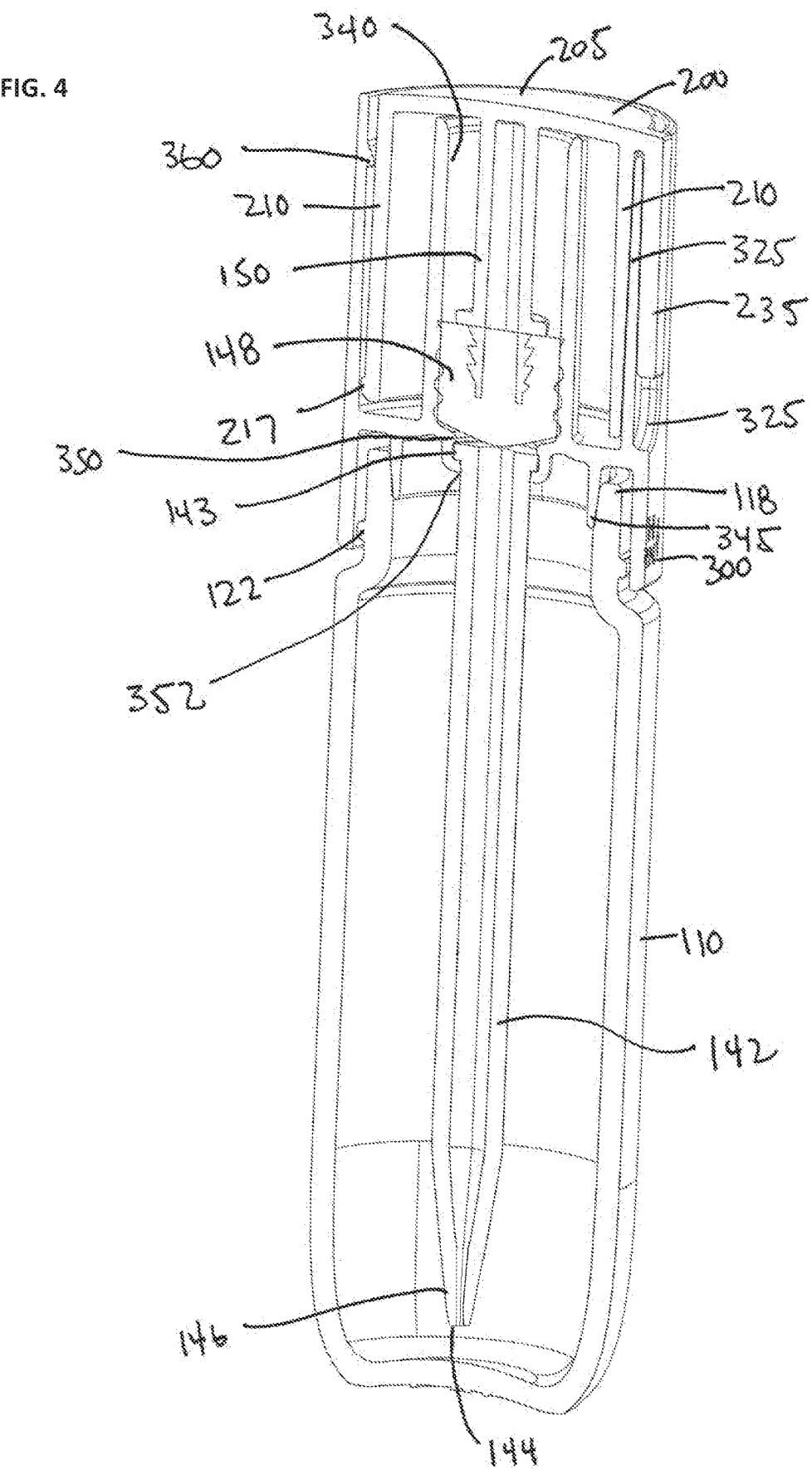
FIG. 4 is a cross section view of the bottle assembly in accordance with an embodiment of the invention.
Figure 5:
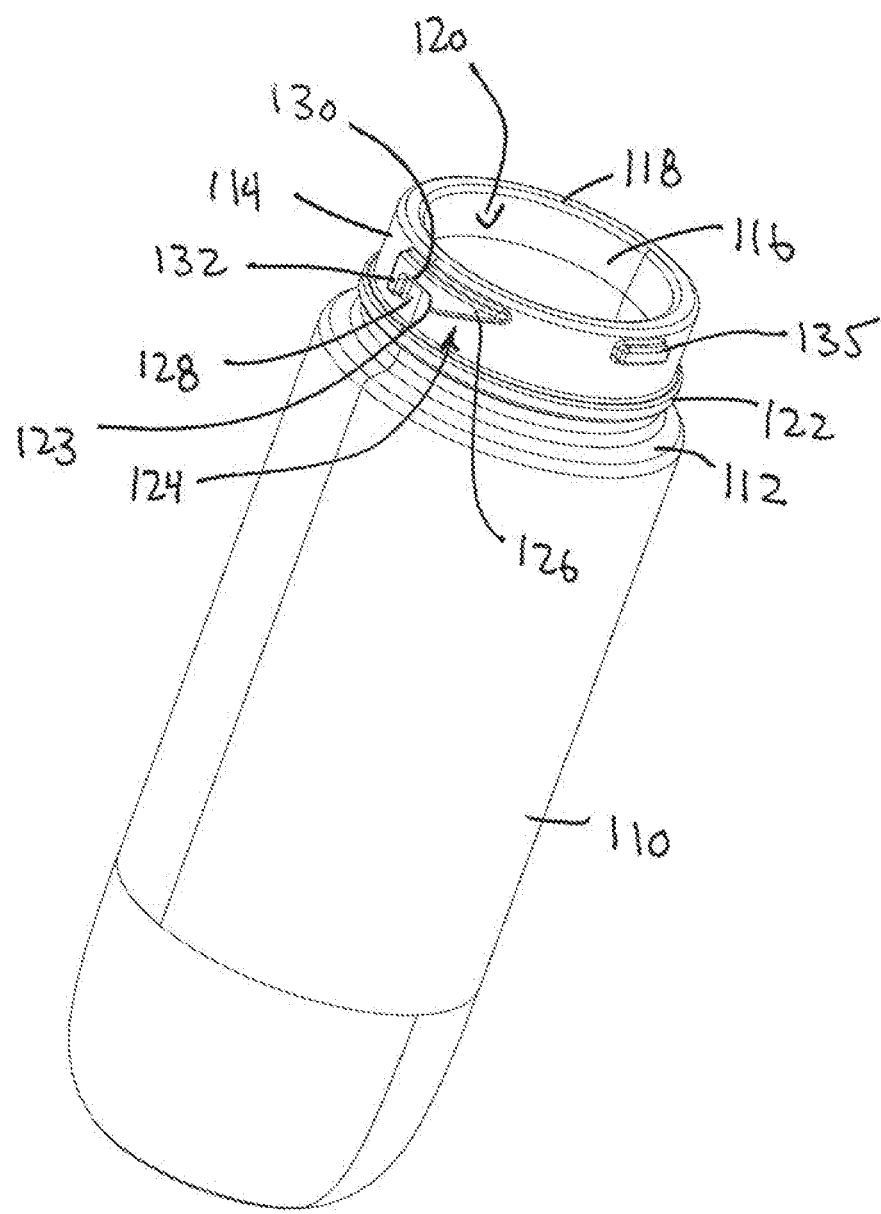
FIG. 5 is a view of a bottle used in a bottle assembly in accordance with an embodiment of the invention.
Figure 6:
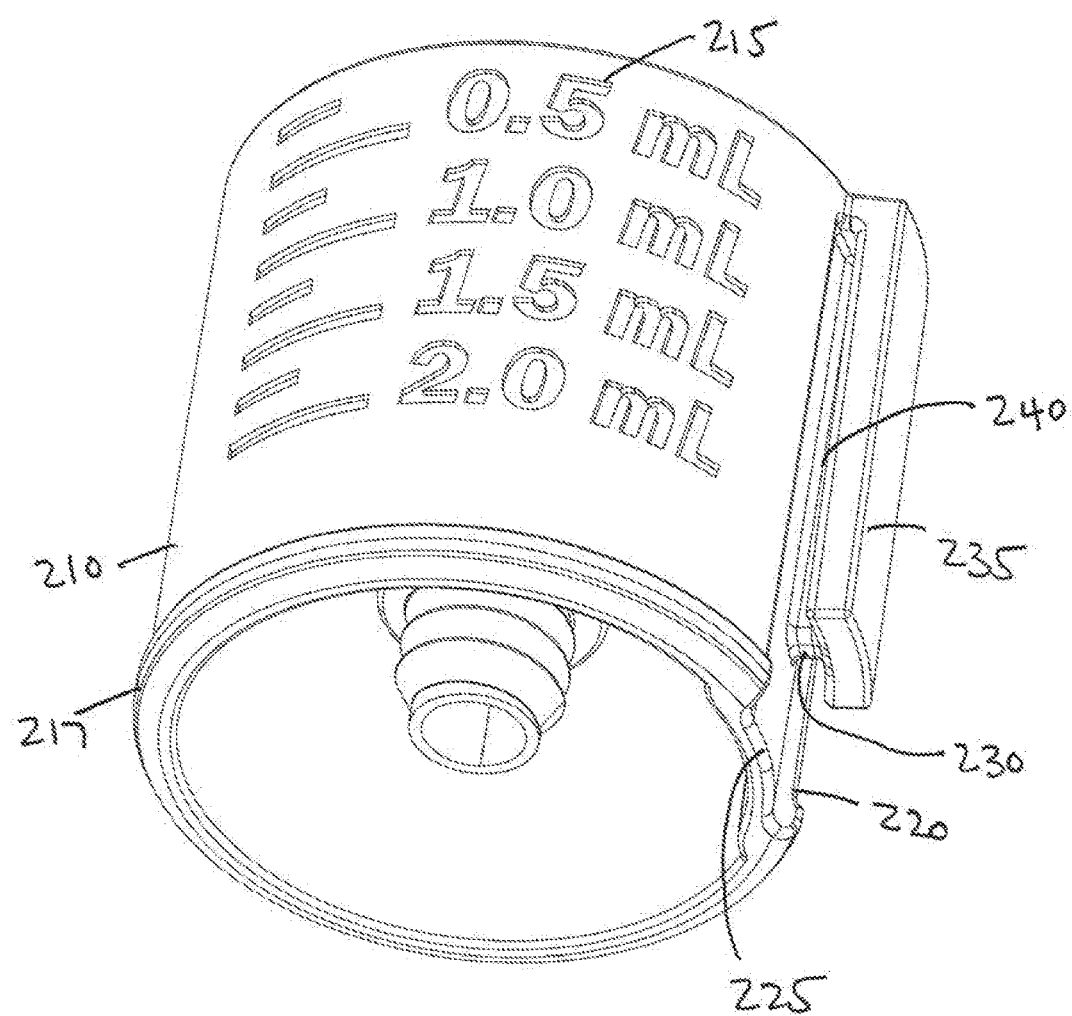
FIG. 6 is a view of the cap used in a bottle assembly in accordance with an embodiment of the invention.
Figure 7:
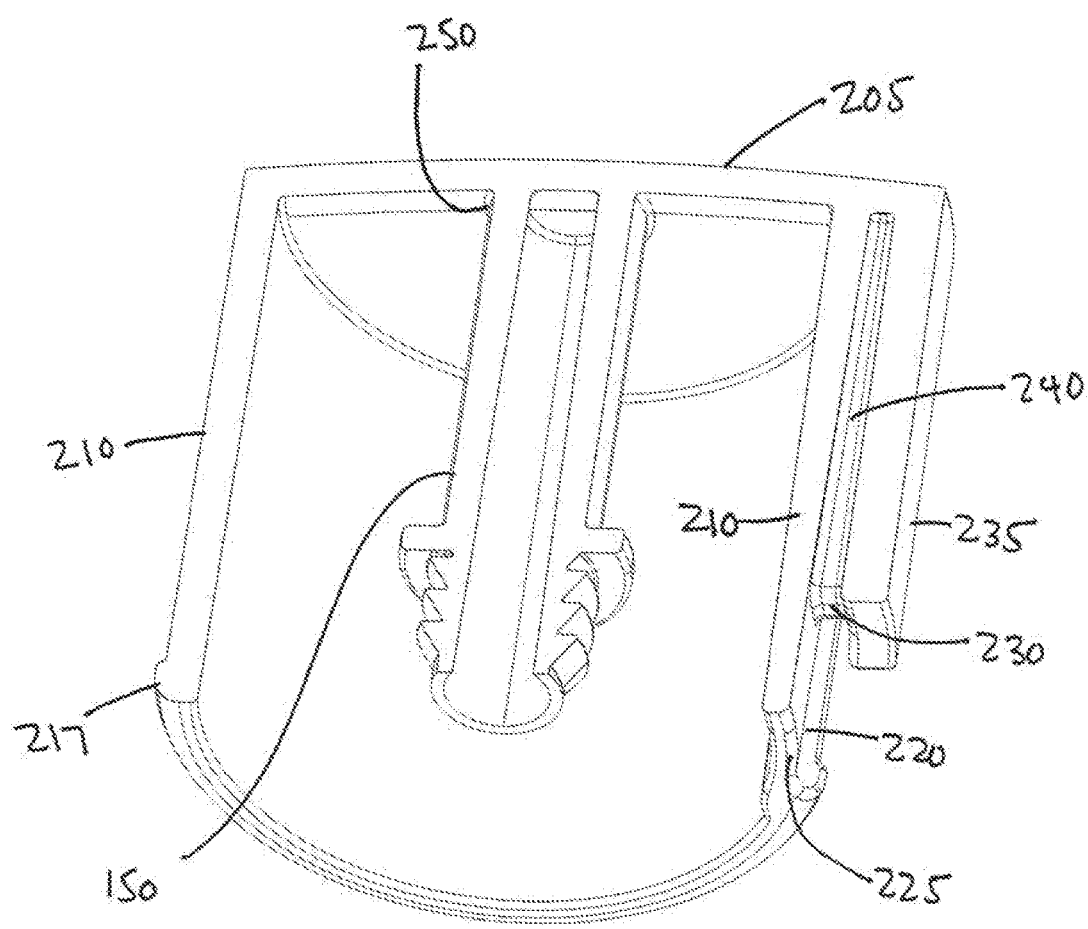
FIG. 7 is a sectional view of the cap from FIG. 6.
Figure 8:
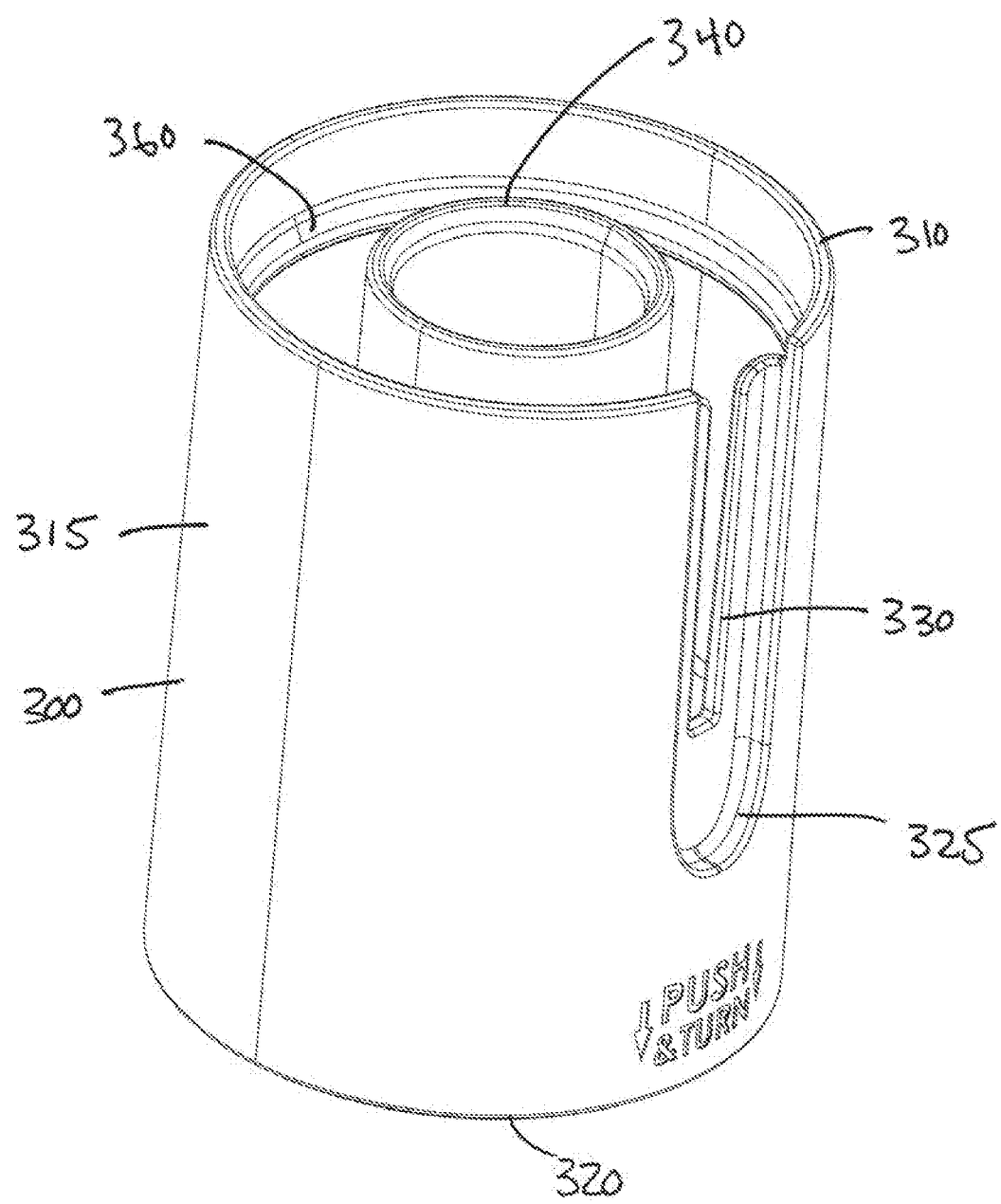
FIG. 8 is a perspective view of a collar used in a bottle assembly in accordance with an embodiment of the invention.
Figure 9:
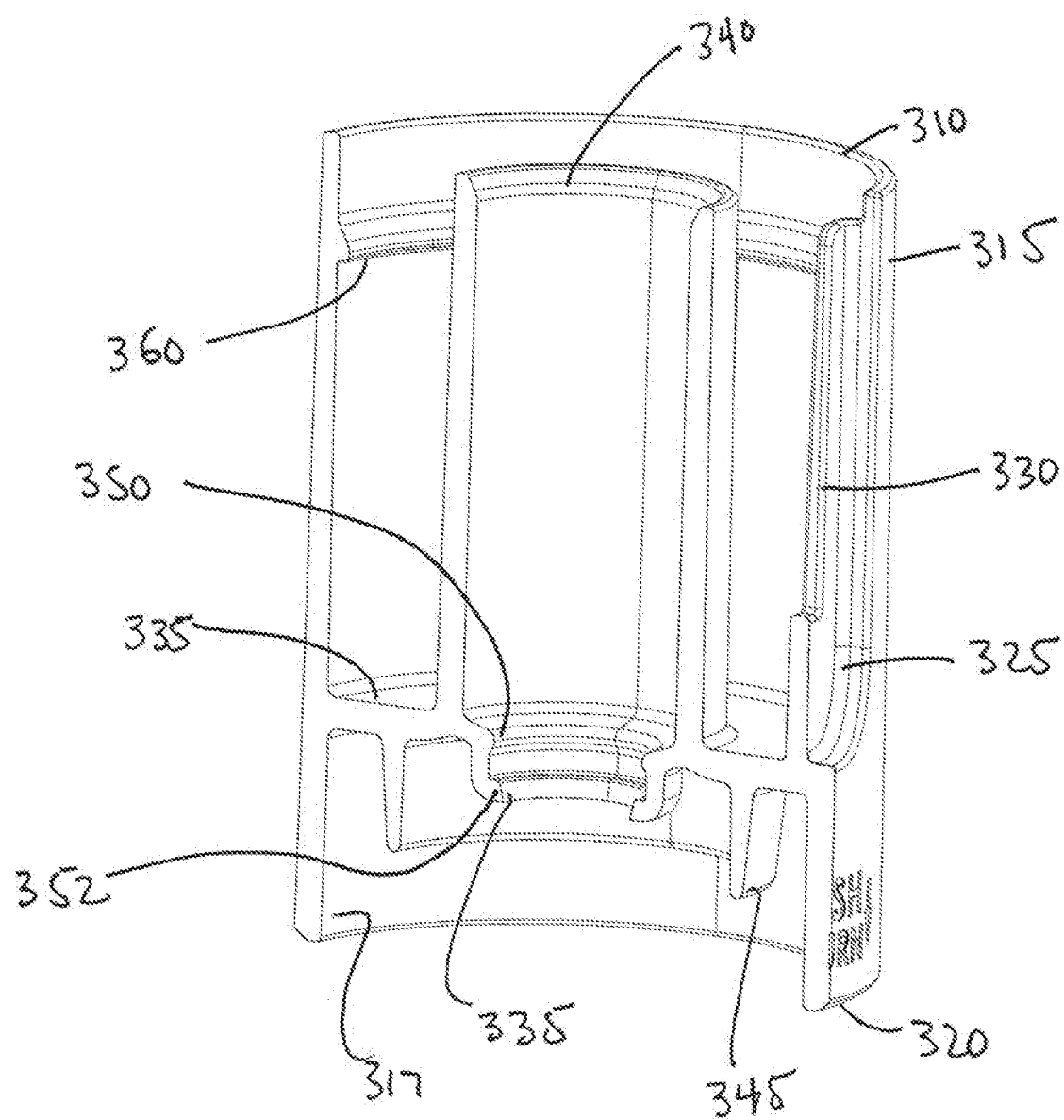
FIG. 9 is a sectional view of the collar from FIG. 8.
Figure 10:
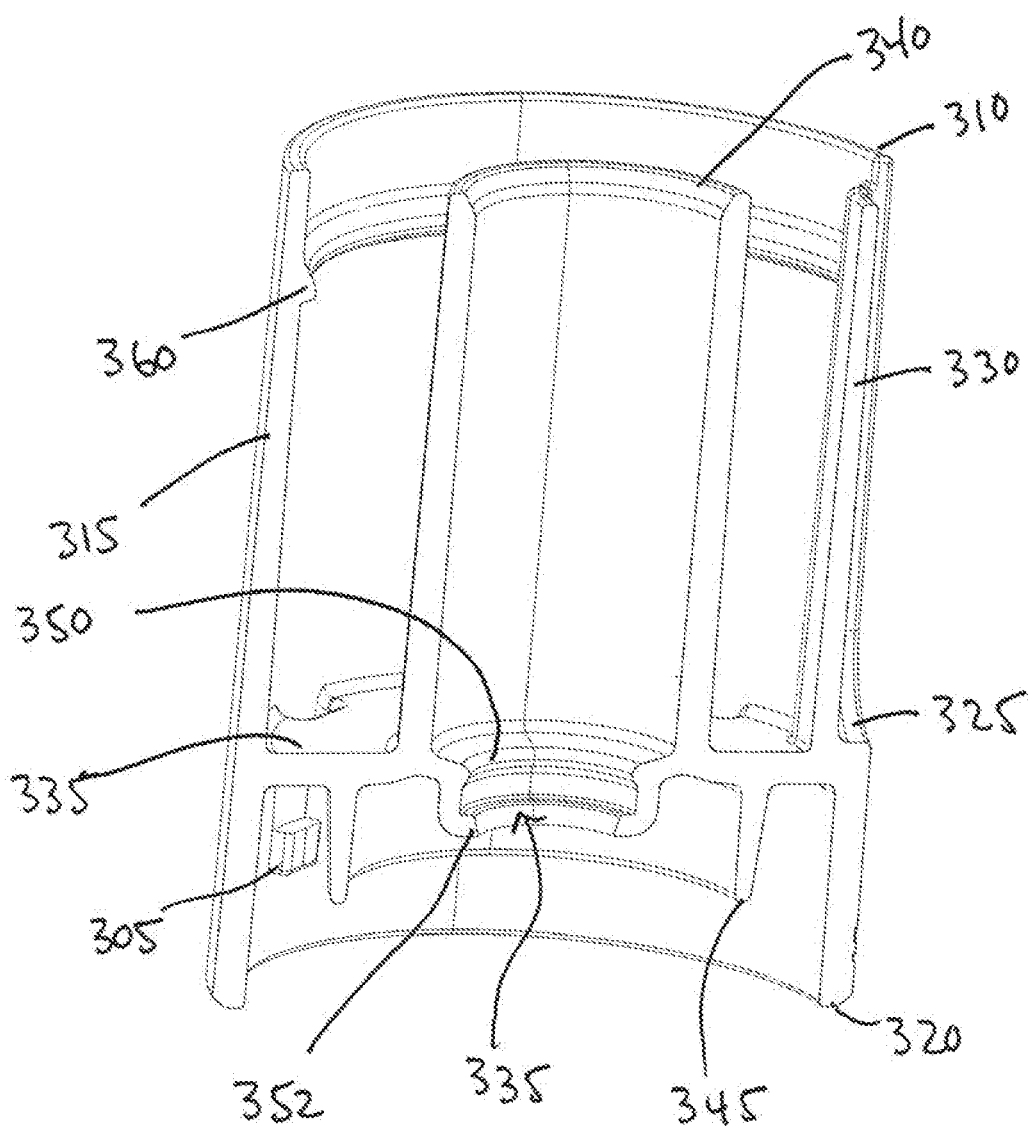
FIG. 10 is another sectional view of the collar from FIG. 8.
Figure 11:
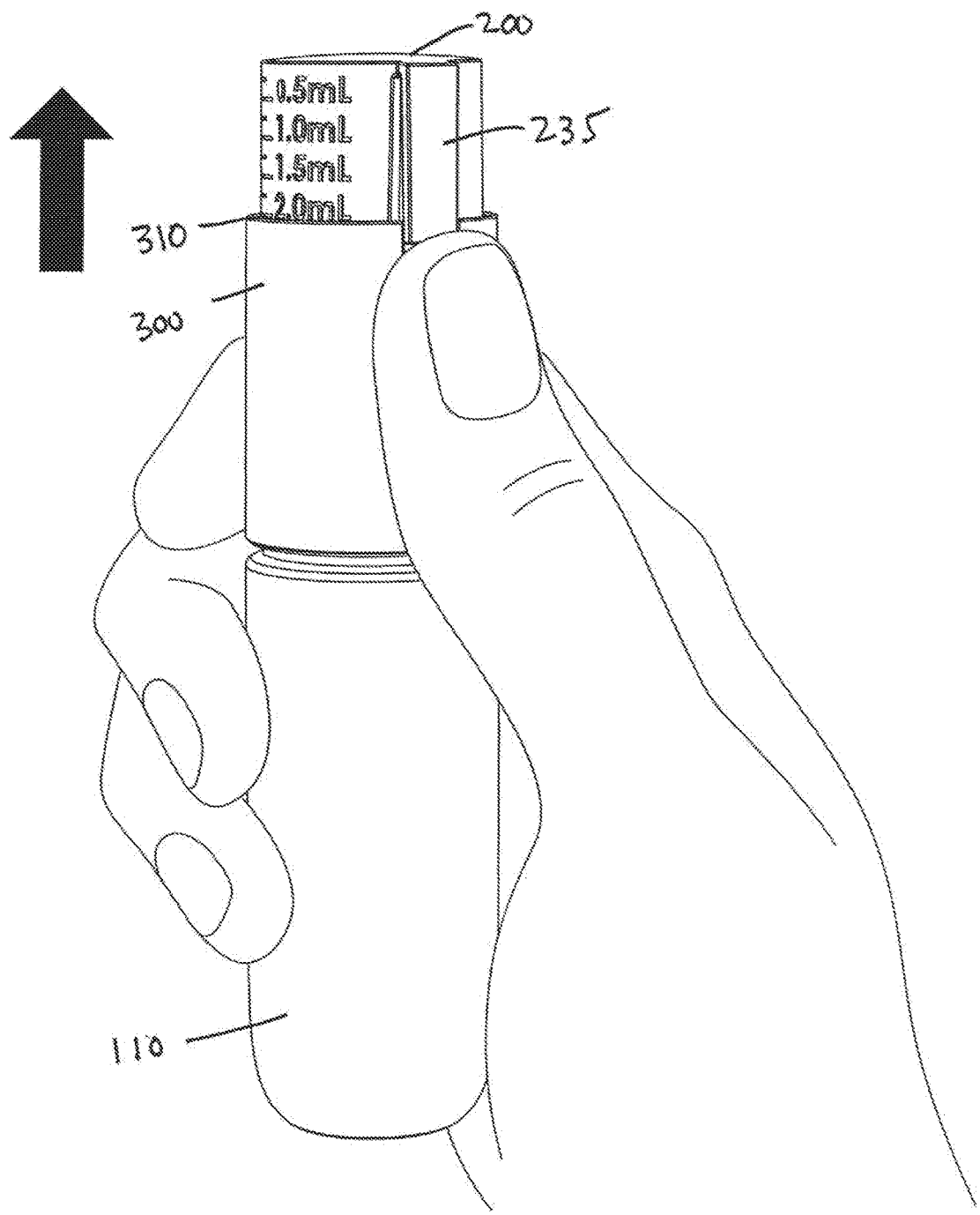
FIG. 11 is an operational view of a bottle assembly in accordance with an embodiment of the invention, illustrating the movement of the cap in relation to the collar.
Figure 12:
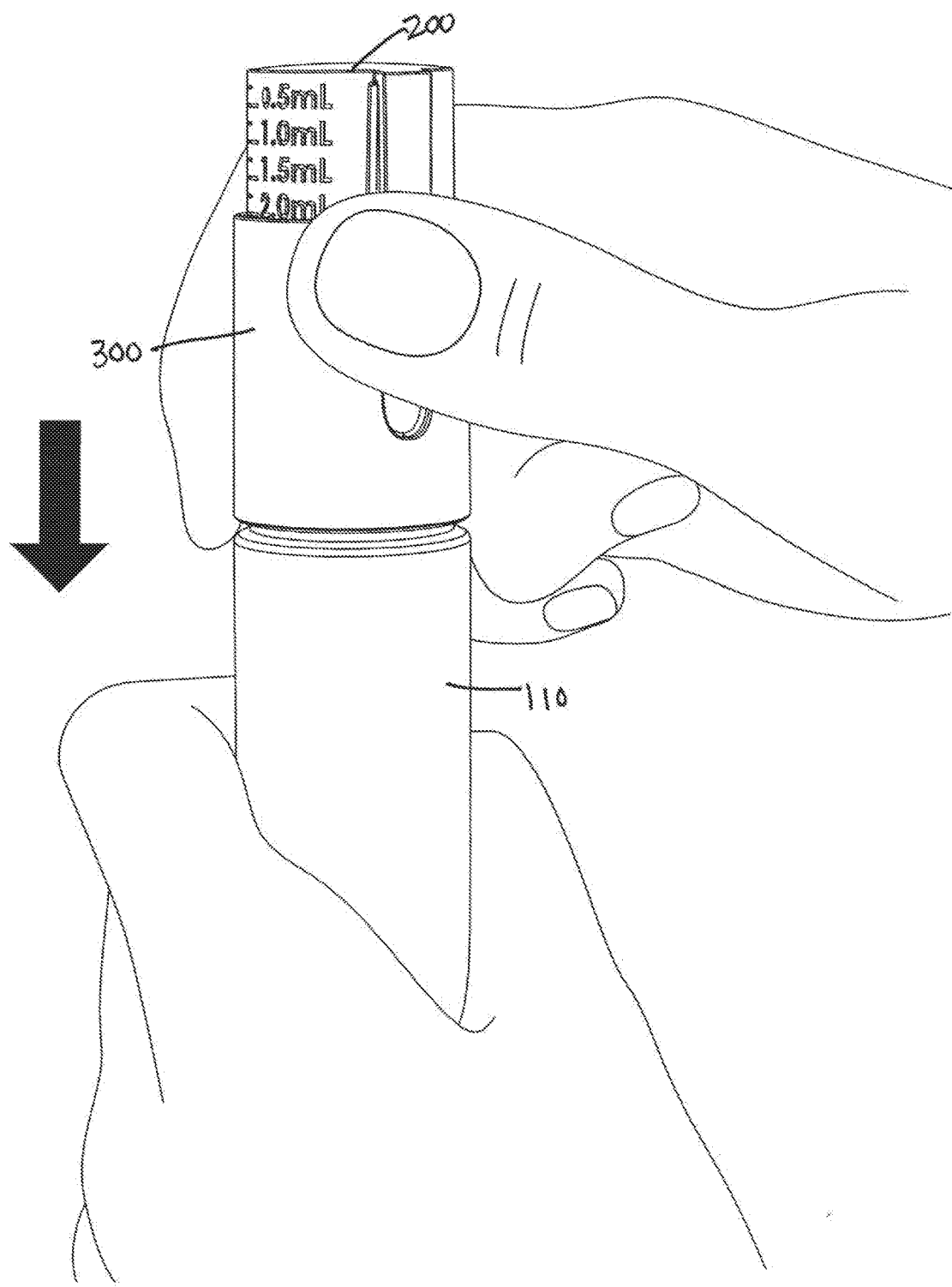
FIG. 12 is an operational view of a bottle assembly in accordance with an embodiment of the invention, illustrating the movement to remove the cap form the bottle.
Figure 13:
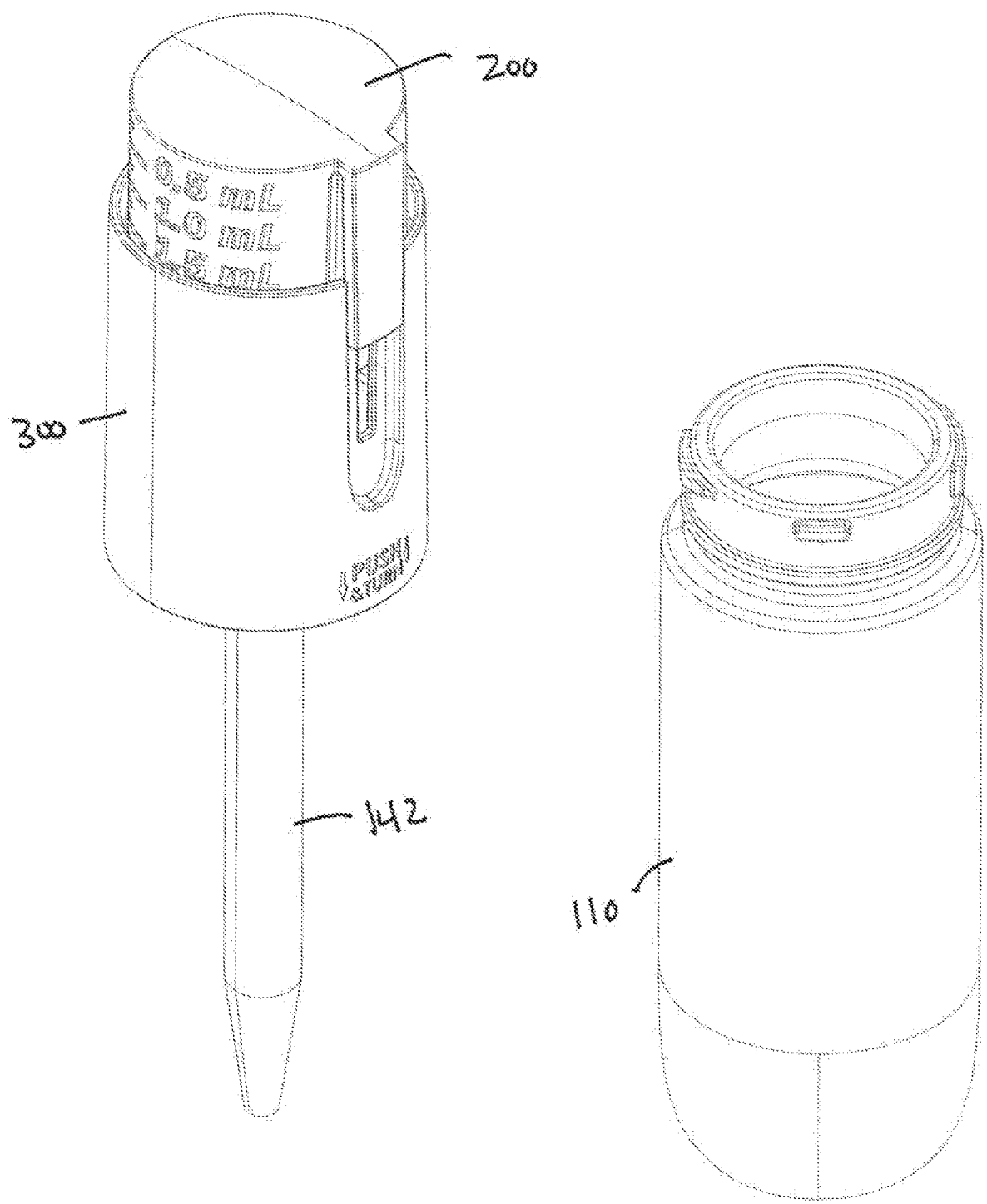
FIG. 13 is a view of the bottle assembly showing the cap removed from the bottle.
Figure 14:
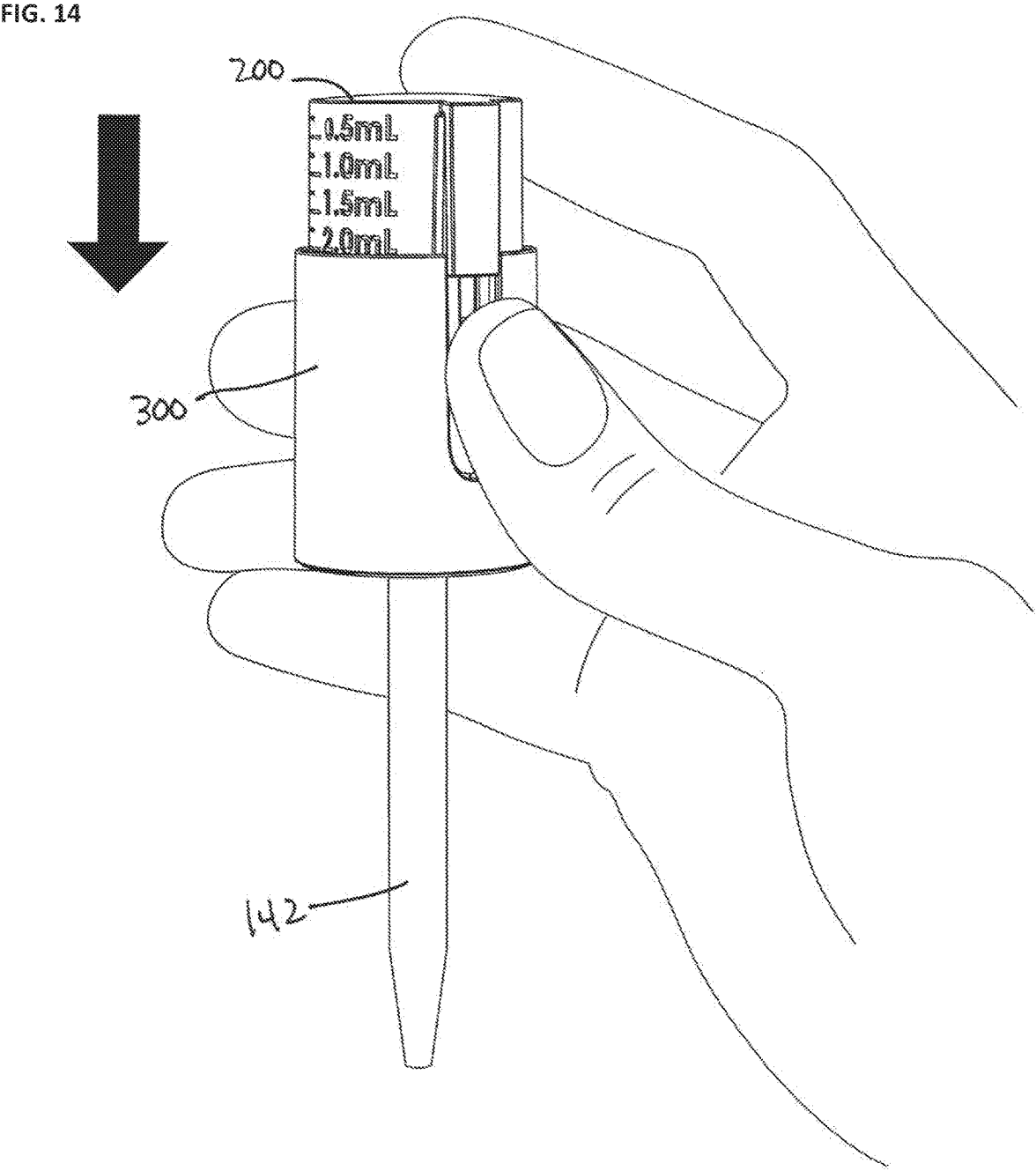
FIG. 14 is an operational view of a bottle assembly in accordance with an embodiment of the invention, illustrating the movement of the cap in relation to the collar to dispense the liquid in a syringe.
Figure 15:
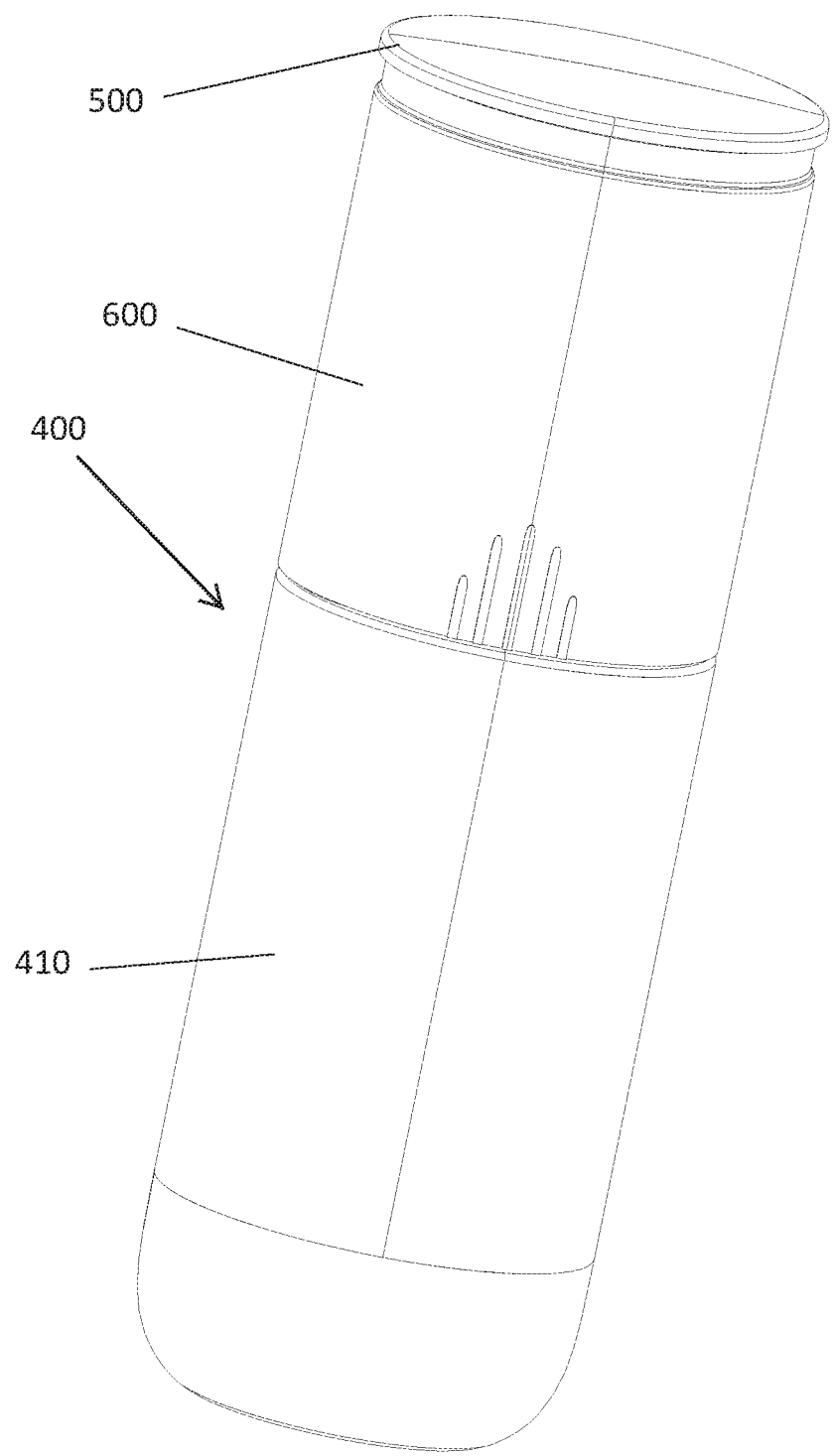
FIG. 15 is a perspective view of another embodiment of a bottle assembly in accordance with an embodiment of the invention.
Figure 16:
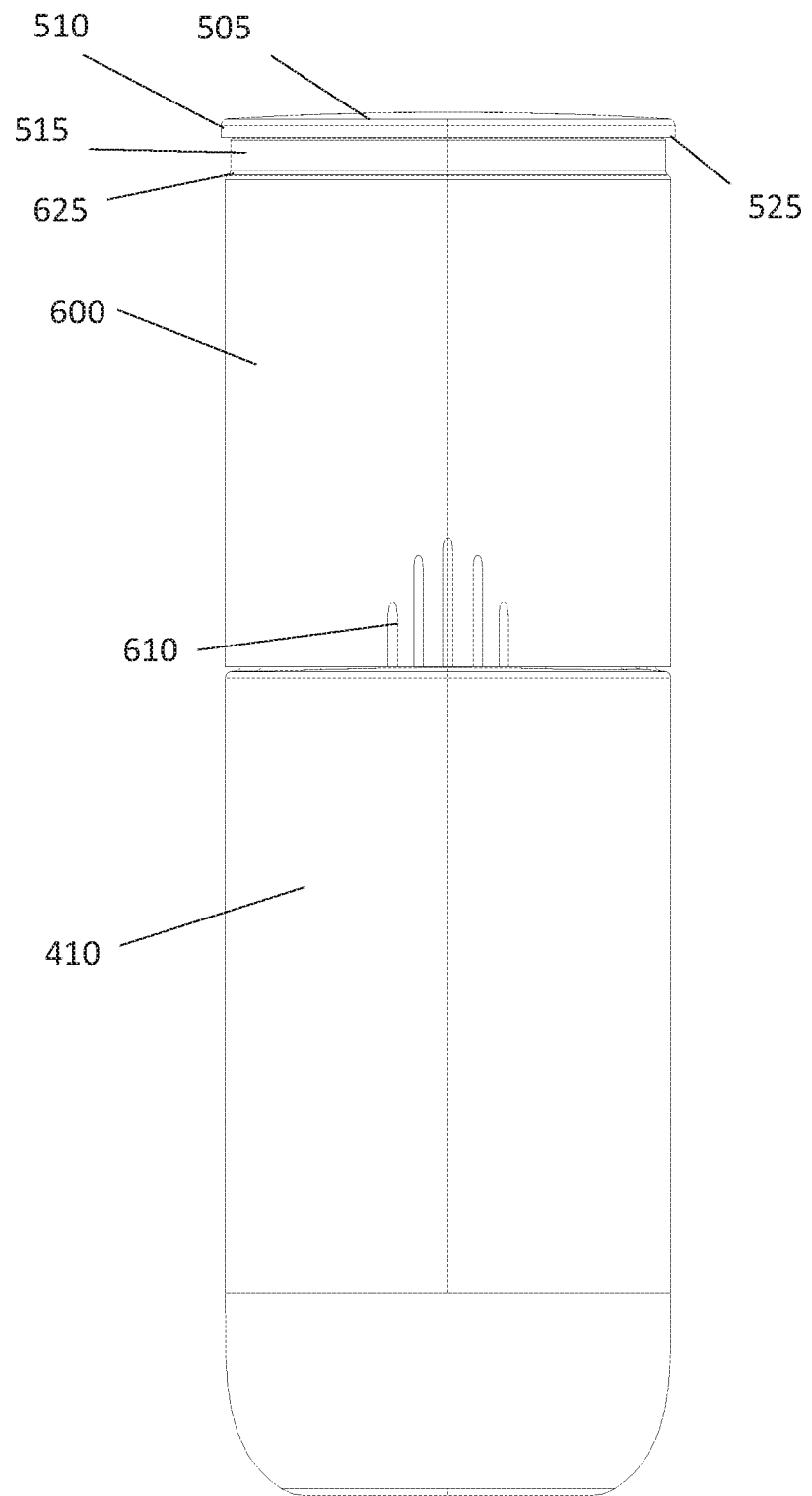
FIG. 16 is a front view of the bottle assembly from FIG. 15.
Figure 17:
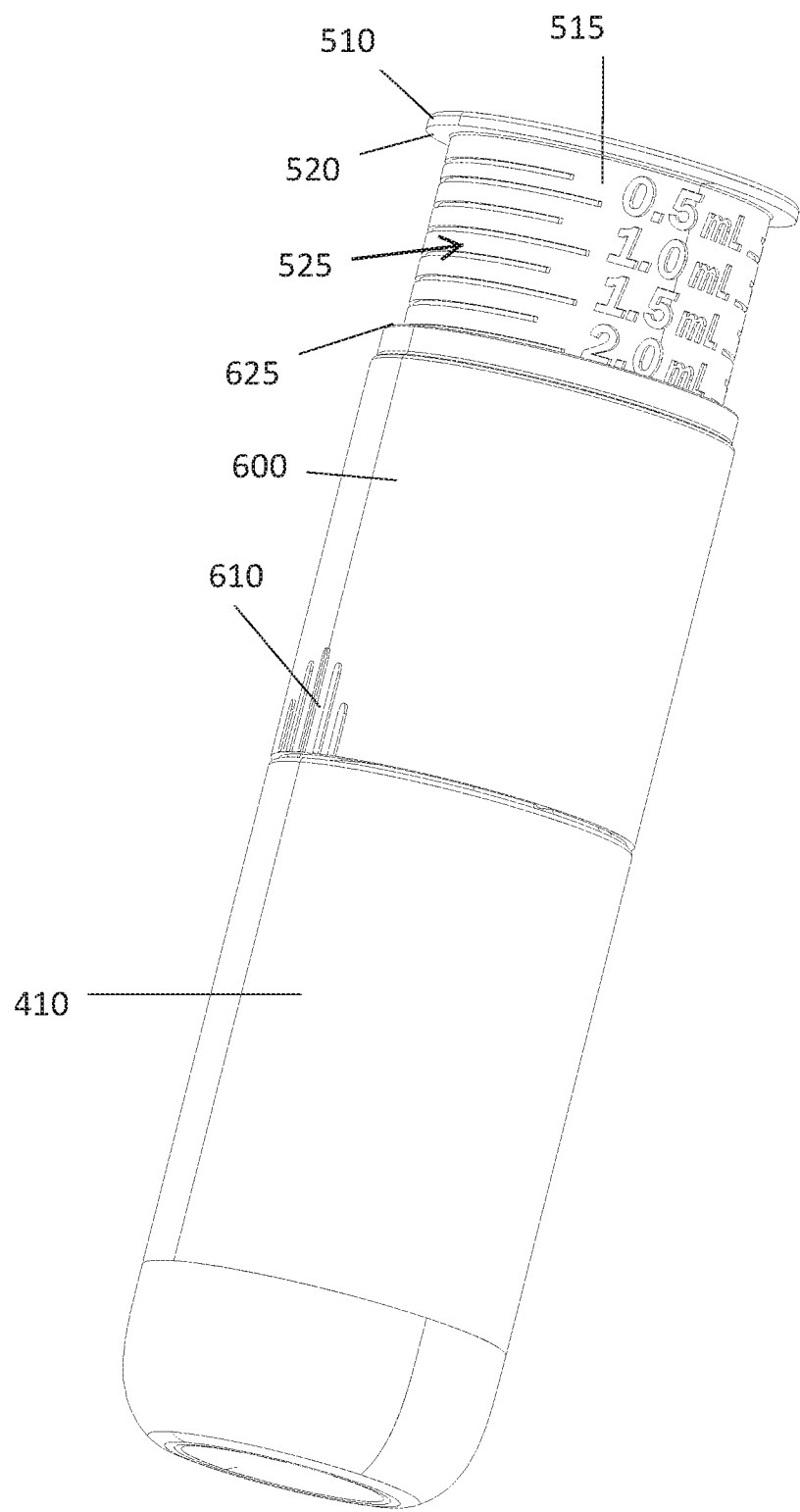
FIG. 17 is a perspective view of the bottle assembly from FIG. 15 illustrating the cap portion bulling pulled out for measuring a dose.
Figure 18:
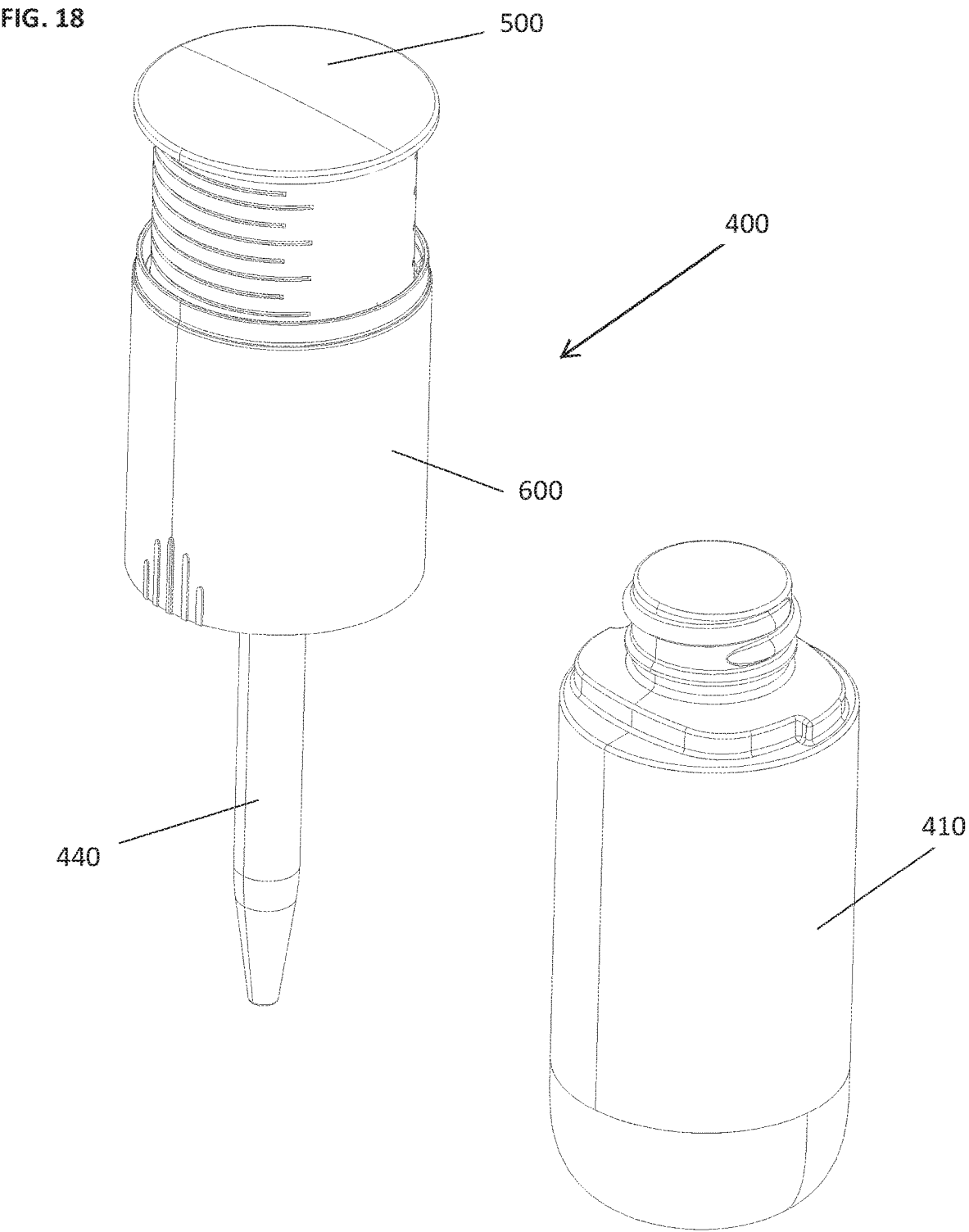
FIG. 18 is a perspective view of the bottle assembly from FIG. 15 illustrating the separation of the cap from the bottle.
Figure 19:
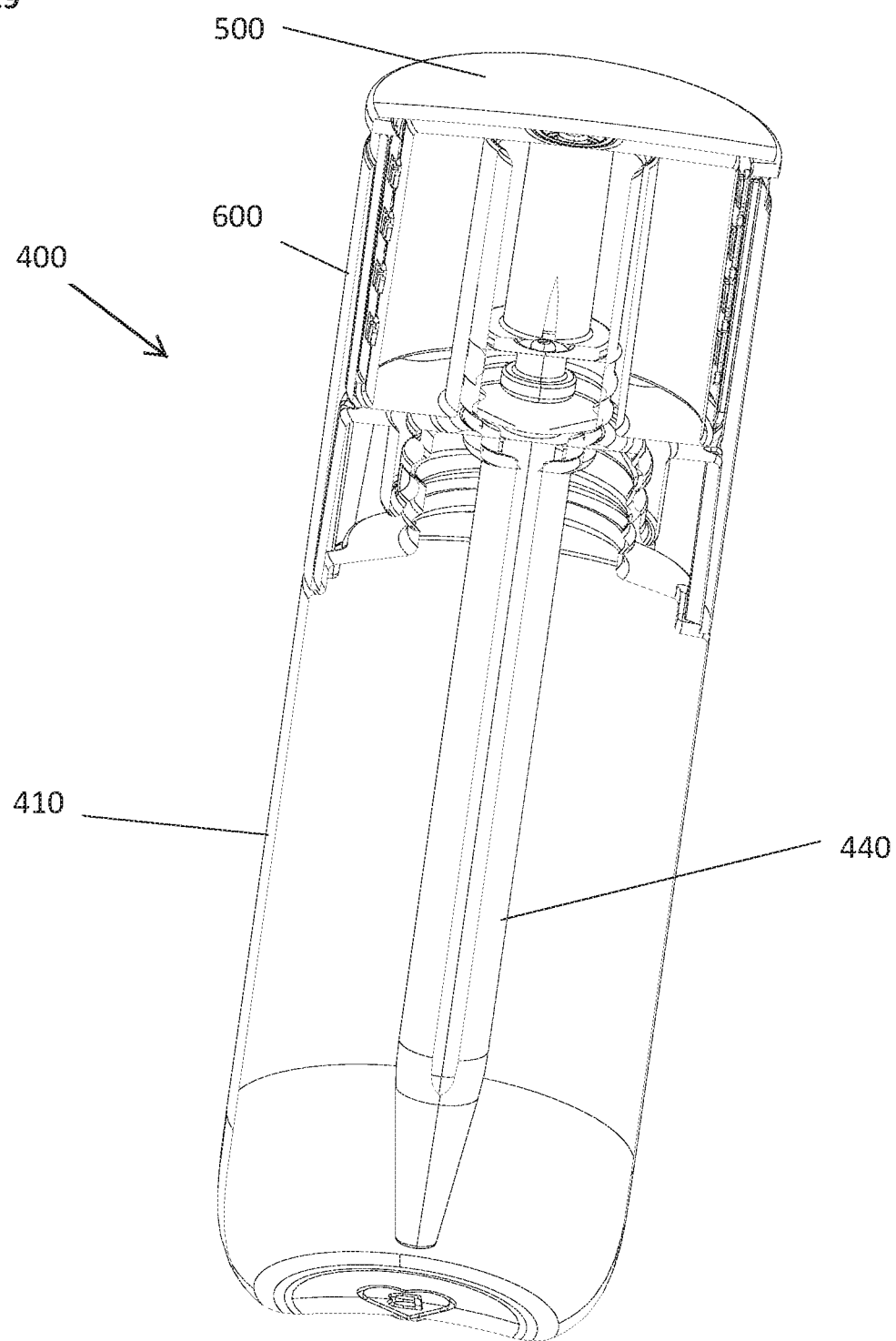
FIG. 19 is a cross section view of the bottle assembly from FIG. 15.
Figure 20:
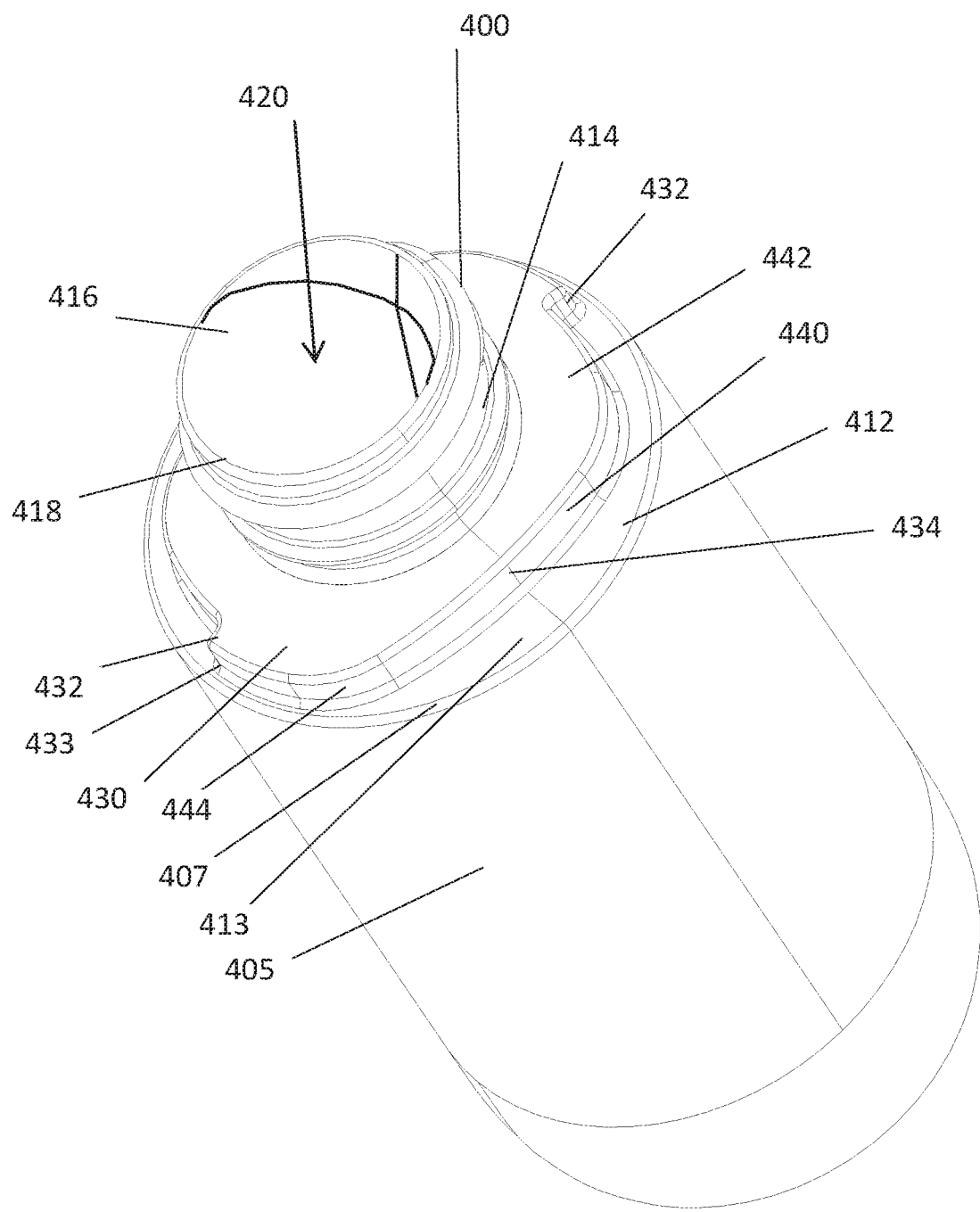
FIG. 20 is a view of the bottle from FIG. 15.
Figure 21:
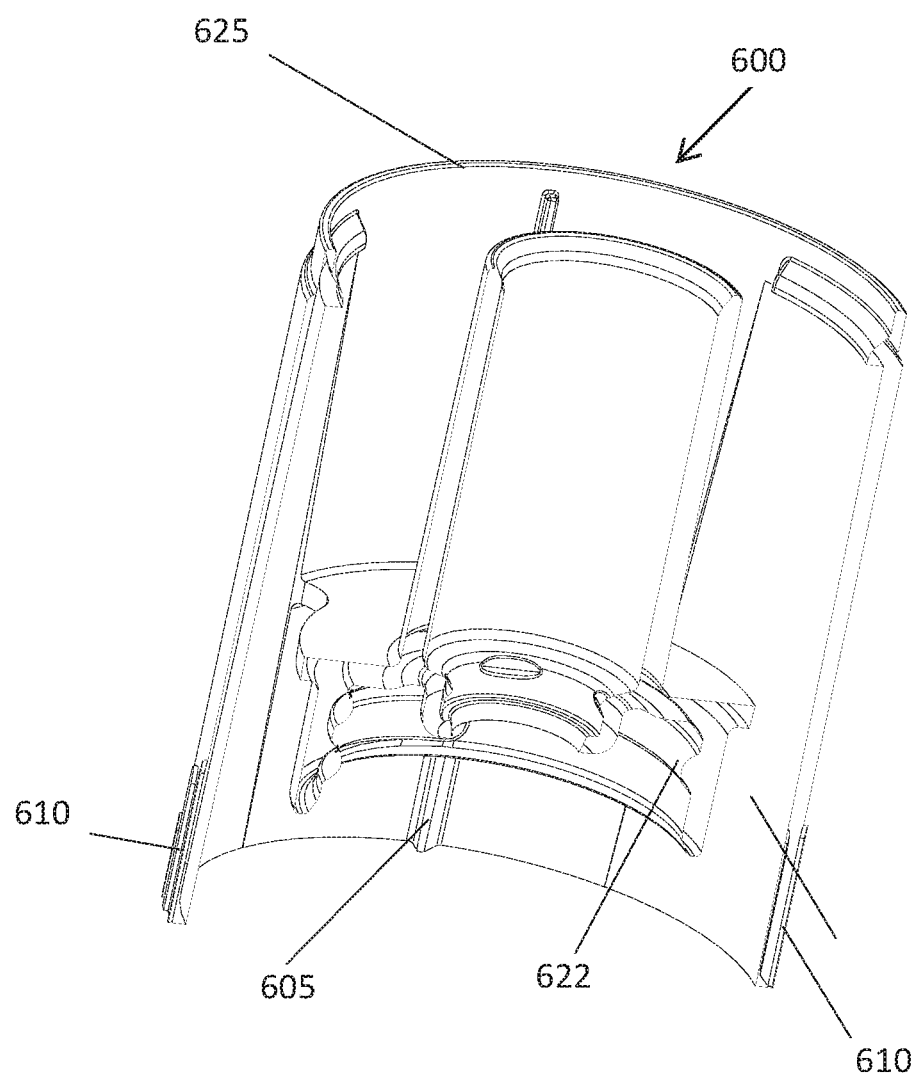
FIG. 21 is a cross section view of a sleeve from the bottle assembly from FIG. 15.
Figure 22:
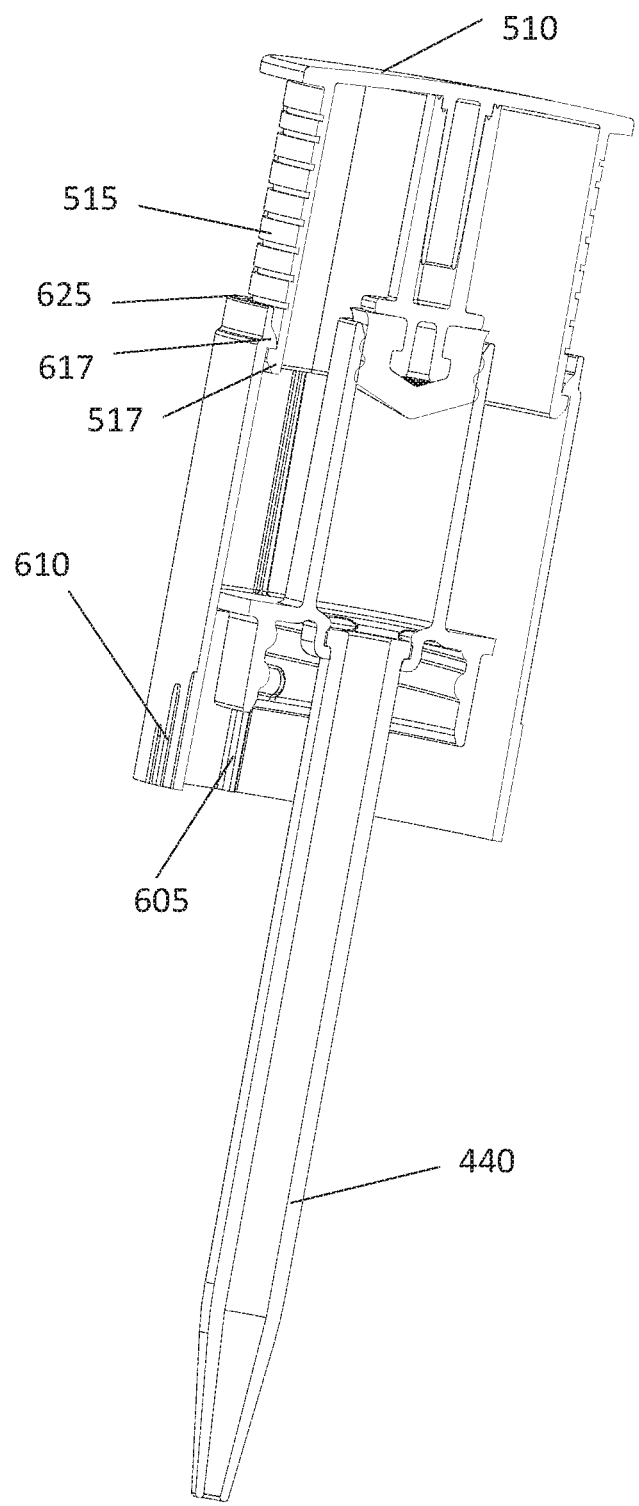
FIG. 22 is a cross section view of the cap assembly with the syringe means for dosing.

Referring now to the figures, namely FIGS. 1 through 14, there is shown a bottle assembly 100 for the storing and dispensing of a liquid which may include forms of medication. The bottle assembly 100 is preferably a child-resistant adult friendly assembly 100, meaning it is difficult for a child to open and easier for an adult to open and dispense. The bottle 100 preferably includes a bottle 110 with a syringe means 140 in communication with a cap 200 and a collar 300.

The bottle 110 includes a shoulder portion 112 leading into a neck portion 114 with a defined opening 116 about an upper rim 118 to create an internal reservoir 120 for the holding of a liquid. The neck portion 114 includes a bottom annual bead 122 and at least two locking lugs 124 positioned on the neck portion 114 between the bottom annular bead 122 and the upper rim 118. The locking lugs 124 are preferably spaced 180° from each other. Each locking lugs 124 includes an entrance ramp 126 tapering downwardly towards the annual bead 122 leading into a channel 128. The channel 128 is positioned slightly higher than an end wall 123 of the entrance ramp 126 to create a seat 130 between end 123 of the entrance ramp 126 and a defined stop wall 132. The locking lugs 124 work in concert with corresponding latches 305 on the inside of the collar 300. To lock the collar 300 in position, the latches are positioned in the seat; while to unlock the collar 300, the collar 300 is pressed down until the latches are below the end wall 123 and twisted to move the latches into the entrance ramp 126 thereby releasing the collar 300 from the bottle 110. The end stop wall 132 extends towards the annular bead 122 to prevent rotation of the collar any further than the end stop wall 132. Additional lugs 135 and latches 305 may be positioned between the locking lugs to help prevent tampering of the collar 300.

The cap 200 has a top base 205 terminating to a side wall 210 that extends downwardly. The side wall 210 includes visual dosage markings 215 on the outside of the cap that are measured against the top rim 310 of the collar 300. As the cap 200 is raised or lowered in relation to the collar 300, the user can measure the dosage within the syringe by visually lining up the dosage markings 215 to the top rim 310 of the collar 300. The side wall 210 further include a bottom lip 217 extending outwardly from the side wall 210. Along one portion 220 of the side wall 210 is an indented section 225 that includes a flange 230 extending along the indented section 225 and attaching to an arm 235. The arm 235 is wider than the flange 230 to create a channel 240 along either side of the flange 230 defined between the indented section 225 and arm 235.

The syringe means 140 is a typical dispensing syringe that draws a liquid within the bottle 110 into a syringe 142 by an opening 144 on the bottom 146 of the syringe 142 and is capable of ejected the same out of the opening 144. The intake and ejection of the liquid occurs with a user manually move the cap 200 in relation to the collar 300. The syringe means 140 further includes a piston plug 148 secured to a piston 150 that is attached to and extends downwardly from an underside 250 of the top base 205 of the cap 200.

The collar 300 includes an external wall 315 extending from the top rim 310 to a bottom rim 320. Along a portion of the external wall 315 is an indented wall section 325 with a slot 330 extending through the external wall 315. The indented wall section 325 and slot 330 are configured to such that the flange 230 sits and slides within the slot 330 with the arm 235 positioned along the outside of the indented wall section 325 of the collar and the side wall 210 of the cap 200 situated on the inside of the collar 330 at the slot 330. The elements are configured to allow the cap 200 to slide up and down in relation to the collar 300, by having a sliding engagement between the flange 230 and slot 330.

Extending inwardly from the inside of the collar 330 is a surface member 335 that connects the external wall 315 to an internal well 335. The internal well 335 has an upstanding well wall 340 and a downwardly extending well wall 345. The upstanding well wall 340 extends upwardly towards the top rim 310 and is configured to receive the piston 150 extending from the cap 200. In addition, the piston plug 148 which is connected to the piston 150 is frinctionally fitted within the upstanding well wall 340 such that movement of the cap out of the collar 300 causes suction within the syringe to draw liquid therein or causes liquid to expel from the syringe 140 when the cap is pressed downwardly into the collar 300.

The downwardly extending well wall 345 is configured to rest within the opening 120 of the bottle 110. The external wall 315 includes an internal surface 317 that is positioned against the outside or neck section 114 of the bottle. The latches 305 are situated on the internal surface 317 and configured as noted to engage the locking lugs 124. In addition, the internal well 335 includes radially inward lips defined as an upper lip 350 and lower lip 352 spaced to engage and capture a head 143 of the syringe 142, The collar 300 further includes a ledge 360 inwardly projection towards the top rim 310 and surface as a stop to the movement of the cap when the cap moves upwardly away to draw liquid into the syringe. The cap will stop moving when the bottom lip 217 extending outwardly from the side wall 210 makes contact with the ledge 360.

In operation, the user presses the cap upwardly from the collar, by pressing up on the arm, usually with a finger. This draws liquid into the syringe. The user further can measure the dosage by visually aligning the markings on the outside of the cap with the edge of the collar. The user then presses the collar down towards the bottle and twists to unlock the collar allowing the cap/collar to be separated from the bottle. To dispense, the user presses the cap down into the collar.

In a second embodiment, there is provided a bottle assembly 400 for the storing and dispensing of a liquid which may include forms of medication. The bottle assembly 400 is preferably a child-resistant adult friendly assembly 400, meaning it is difficult for a child to open and easier for an adult to open and dispense. The bottle assembly 400 preferably includes a bottle 410 with a syringe means 440 in communication with a cap 500 and a collar 600.

The bottle 410 includes a bottle wall 405 extending up to a bottle wall edge 407 that terminates to a shoulder portion 412 leading into a neck portion 414 with a defined opening 416 about an upper rim 418 to create an internal reservoir 420 for the holding of a liquid. The neck portion 414 includes external threads 422 which cooperate with internal threads 622 on the collar 600. The shoulder portion 412 includes a raised upper facing base 430. The upper facing base 430 includes a pair of opposing side stops 432 (that are oppositely facing) and a pair of opposing detents 434. The detents and side stops alternate around the upper facing base such that one side stop is positioned between the two opposing detents, preferably but not necessarily at 90° from each other (or 180° between two opposing side stops or two opposing detents). Each side stop 432 includes an outward flange 433 that are positioned adjacent to or along the bottle wall edge 407 and the pair of opposing detents 434 are positioned inwardly along the shoulder portion away from the bottle wall edge 407 creating a ledge 413 between the edge of the shoulder portion 412 and the edge of the bottle wall edge 407. The raised upper facing base 430 on the shoulder portion 412 includes a vertical wall surface 440 from the shoulder portion 412 to the top 442 of the upper facing base 430. The vertical wall surface 440 includes a tapered or ramp profile 444 leading from the detents 434 towards the side stops 432. The ramp profile 444 allows the user to screw the cap on until the vertical rib roll over the ramp profile and position on the other side of the side stops 432. Counter rotation is prevented by the side stops unless the user presses the collar along the detents. As explained further below the positions of the detents and side stops are provided to work in concert with the collar 600 to provide for the child-resistant senior friendly opening.

To lock/unlock the collar 600 in position, the collar 600 include a pair of internally extending vertical ribs 605, positioned 180° from each other in the opposing detents 434. When the collar is rotated, the ribs will make contact with the side stops 432 preventing the removal of the collar/cap/syringe means. To unlock and remove, the user squeezes opposing sides of the collar, along external indicators 610, which align with the detents 434. When squeezed, the collar deforms such that the vertical ribs deflect out away from the side stops allowing the user to rotate the collar off of the bottle. The side stops prevent the rotation of the collar off of the bottle unless sides are squeezed.

The cap 500 has a top base 505 terminating to a top base edge 510. A top side wall 515 extends downwardly from beneath the top base edge such that there is an indented rim 520 under the top base edge around the periphery of the top base 505. This allows the user to pull or push the top base 505 of the cap 500 upwardly, which draws liquid into the syringe means.

The top side wall 515 includes visual dosage markings 525 that are used to measure dosage. As the cap 500 is raised or lowered in relation to the collar 600, the user can measure the dosage within the syringe by visually lining up the dosage markings 525 to a top rim 625 of the collar 600.

The top side wall 515 further include a bottom lip 517 extending outwardly from the side wall. Conversely, the collar 600 includes an inwardly extending upper lip 617 near the top rim 625 of the collar 600. When assembled, the bottom lip and upper lip work in concert to prevent the separation of the cap from the collar.

The syringe means is as described with respect to the first embodiment. In addition, any elements from the first embodiment similarly designed are imported into the second embodiment without further explanation.

In operation, the user pulls the cap upwardly from the cap top drawing liquid into the syringe. The user further can measure the dosage by visually aligning the markings on the outside of the cap with the edge of the collar. The user then squeezes the collar along predetermined indicators and then twists to unlock the collar allowing the cap/collar to be separated from the bottle. To dispense, the user presses the cap down into the collar.

From the foregoing and as mentioned above, it is observed that numerous variations and modifications may be effected without departing from the spirit and scope of the novel concept of the invention. It is to be understood that no limitation with respect to the embodiments illustrated herein is intended or should be inferred. It is intended to cover, by the appended claims, all such modifications within the scope of the appended claims.

We claim:

1. A child-resistant adult-friendly bottle assembly to dispense a liquid, the bottle assembly comprising:
    a bottle having a bottle wall extending from a bottle base to a shoulder portion which terminates into a neck portion, the neck portion defining an opening about an upper rim to create an internal reservoir for holding a liquid;
    a cap and collar assembly having a cap and a collar, the cap and collar assembly configured such that a portion of the cap is secured within the collar and vertically movable in relation to the collar;
    a child-resistant adult-friendly retention configuration configured to removably attach the cap and collar assembly to the neck portion of the bottle, the retention configuration defined by having:
        a pair of vertical ribs being positioned on an inside portion of the collar;
        a pair of vertical side stops positioned on top of the shoulder portion of the bottle and separately corresponding to the pair of vertical ribs, and wherein each vertical side stop includes an entrance ramp starting along a detent positioned away from the vertical side stop and tapering outwardly towards the each one of the vertical side stops, whereby the collar locks when rotated such that the vertical ribs are positioned against the vertical side stops and the collar and cap assembly is removably from the bottle when the collar is pressed inwardly along the detents to deflect the vertical ribs outwardly such that rotation and removal of the collar is permitted, and wherein movement of the collar and cap assembly is separate from movement of the vertical movement of the cap in relation to the collar portion;
    a syringe means secured to the cap, the syringe means having a syringe tube positioned within the bottle when the cap and collar assembly is attached to the bottle, the syringe means configured to draw a liquid from the bottle when the cap is vertically moved away from the collar and the cap and collar assembly is attached to the bottle, and further configured to expel a liquid from the syringe tube when the cap is vertically moved towards the collar either when the cap and collar assembly is attached to the bottle or unattached to the bottle; and
    dosage marking indicia positioned downwardly along the cap and viewable on the outside of the cap as the cap is vertically moved in relation to the collar and wherein a dosage of liquid within the syringe tube is configured to match the dosage marking indicia as the cap is vertically moved and the dosage marking indicia aligns with a top rim of the collar.

2. The child-resistant adult-friendly bottle assembly of claim 1, wherein the cap includes:
    a top base terminating to a top base edge; a top side wall extends downwardly from beneath the top base edge such that there is an indented rim under the top base edge around the periphery of the top base, wherein the top base is pushed and pulled from under the top base edge to move the cap upwardly and downwardly in relation to the collar which draws liquid into the syringe means and expels liquid out of the syringe means.

3. The child-resistant adult-friendly bottle assembly of claim 2, wherein the collar comprising:
    an external cylindrical wall extending from a top rim to a bottom rim;
    a top ledge projecting inwardly from an internal surface of the external cylindrical wall and being positioned towards the top rim, and wherein the cap is vertically movable in relation to the collar and wherein the top ledge of the external cylindrical wall and the bottom lip cooperate as an upper limit of movement between the cap and collar;
    a surface member extending inwardly from the external cylindrical wall, and wherein the surface member and the bottom rim cooperate as a lower limit of movement between the cap and collar.

4. The child-resistant adult-friendly bottle assembly of claim 2, wherein the collar further comprising:
    an upstanding well wall and a downwardly extending well wall both extending from the surface member and defining an internal well opening within the upstanding and downwardly extending well walls;
    wherein the downwardly extending well wall is configured to rest within the opening of the bottle;
    wherein the internal well includes radially inward lips defined as an upper lip and lower lip spaced to engage and capture a head defined on a top portion of the syringe tube; and
    wherein the upstanding well wall is configured to receive a piston and frictionally fit a piston plug such that movement of the cap and thus piston and piston plug within the upstanding well wall draws and expel liquid from the syringe tube.

5. The child-resistant adult-friendly bottle assembly of claim 1, wherein the syringe means is configured to draw and expel a liquid as the cap is vertically moved in relation to the collar, the syringe means having a syringe tube with an opening configured to rest within the bottle to draw and expel a liquid; a piston extending downwardly from an underside portion of the top base of the cap; and a piston plug secured to the piston.

* * * * *